(12) United States Patent
Breuer et al.

(10) Patent No.: US 8,406,537 B2
(45) Date of Patent: Mar. 26, 2013

(54) COMPUTED TOMOGRAPHY SYSTEM WITH DATA COMPRESSION AND TRANSFER

(75) Inventors: Brian Joseph Breuer, Allenton, WI (US); Roy-Arnulf Helge Nilsen, Waukesha, WI (US); Steven John Woloschek, Franklin, WI (US); Scott David Slavic, Sussex, WI (US); Naveen Stephen Chandra, Kenosha, WI (US); Paavana Sainath, Oconomowoc, WI (US)

(73) Assignee: General Electric Company, Schenectady, NY (US)

( * ) Notice: Subject to any disclaimer, the term of this patent is extended or adjusted under 35 U.S.C. 154(b) by 308 days.

(21) Appl. No.: 12/641,109

(22) Filed: Dec. 17, 2009

(65) Prior Publication Data

US 2011/0150171 A1    Jun. 23, 2011

(51) Int. Cl.
  *G06K 9/36* (2006.01)
  *G06K 9/00* (2006.01)
(52) U.S. Cl. ............ 382/232; 382/131; 378/19
(58) Field of Classification Search ............ 378/19; 382/232

See application file for complete search history.

(56) References Cited

U.S. PATENT DOCUMENTS

| 4,982,415 | A  | * | 1/1991  | Shibata et al. ............ 378/15 |
| 5,666,487 | A  | * | 9/1997  | Goodman et al. ........ 709/246 |
| 6,327,330 | B1 | * | 12/2001 | Peter ............... 378/19 |
| 6,697,930 | B2 | * | 2/2004  | Wise et al. ............ 712/2 |
| 7,254,210 | B2 |   | 8/2007  | Popescu |
| 2005/0220353 | A1 | * | 10/2005 | Karczewicz et al. ..... 382/238 |
| 2005/0238137 | A1 | * | 10/2005 | Popescu ............ 378/19 |
| 2006/0094959 | A1 | * | 5/2006  | Lin et al. ............ 600/437 |
| 2007/0280405 | A1 | * | 12/2007 | Krumme et al. ........ 378/4 |
| 2009/0046913 | A1 | * | 2/2009  | Chandra ............ 382/131 |
| 2009/0147908 | A1 | * | 6/2009  | Garms ............ 378/4 |
| 2010/0128949 | A1 | * | 5/2010  | Wegener et al. ....... 382/131 |
| 2010/0128998 | A1 | * | 5/2010  | Wegener et al. ....... 382/248 |

* cited by examiner

*Primary Examiner* — Alexander H Taningco
(74) *Attorney, Agent, or Firm* — Fletcher Yoder, P.C.

(57) ABSTRACT

A computed tomography (CT) system that includes a rotational gantry and a stationary structure communicatively coupled to the rotational gantry is provided. The rotational gantry includes an X-ray source configured to emit an X-ray beam through a subject, an X-ray detector comprising one or more detector elements that receive incoming X-rays and to convert the incoming X-rays to image signals, and a data acquisition unit that processes the image signals to generate processed image data. The stationary structure is coupled to the rotational gantry via one or more slip rings that transfer the processed image data from the rotational gantry to stationary memory integral with the stationary structure via a bidirectional serial data exchange protocol.

20 Claims, 3 Drawing Sheets

COMPUTED TOMOGRAPHY SYSTEM WITH DATA COMPRESSION AND TRANSFER

BACKGROUND OF THE INVENTION

Computed tomography (CT) imaging systems have become ubiquitous in the fields of medical diagnostics and treatment. CT systems typically include an X-ray source, such as a conventional X-ray tube, positioned in a diametrically opposed location from a detector. The source and detector rotate on a gantry, and the source produces beams of X-ray radiation that are directed through a subject of interest and impact the detector on the opposite side of the gantry. The emitted radiation is attenuated by features and structures of the subject, and the transmitted radiation is measured by the detector. Such CT systems use acquired data to reconstruct images of internal features of a variety of subjects, including human and animal patients in a medical diagnostic context, internal configurations and components of parts and parcels, and so forth.

Conventional CT systems rotate at increasingly high speeds to improve the resolution of the resulting reconstructed images. Such high speeds have increased the quantity of image data that is acquired during the CT scan. However, these high speed CT systems utilize slip rings to transfer data from the rotating gantry to permanent disk drives (or other memory circuits) located in a stationary computer. Unfortunately, such slip rings are often costly and unreliable. Moreover, as the quality of data to be transferred increases (with increased rotational speed, increased coverage, etc.), the ability to transmit data through the slip rings becomes a bottleneck in the acquisition and processing of image data. Accordingly, there exists a need for improved CT systems that reduce the cost and unreliability of the data transfer from the rotating gantry to the stationary computer.

BRIEF DESCRIPTION OF THE INVENTION

In one embodiment, a computed tomography (CT) system includes a rotational gantry. The rotational gantry includes an X-ray source configured to emit an X-ray beam through a subject, an X-ray detector comprising one or more detector elements that receive incoming X-rays and to convert the incoming X-rays to image signals, a data acquisition unit comprising data reduction circuitry that performs lossy compression of the image signals to generate compressed image data, and a non-volatile memory device that stores the compressed image data. The CT system also includes a stationary structure communicatively coupled to the rotational gantry via one or more slip rings that transfer the compressed image data from the rotational gantry to stationary memory integral with the stationary structure.

In another embodiment, a computed tomography (CT) system includes a rotational gantry. The rotational gantry includes an X-ray source configured to emit an X-ray beam through a subject, an X-ray detector comprising one or more detector elements that receive incoming X-rays and to convert the incoming X-rays to image signals, and a data acquisition unit that processes the image signals to generate processed image data. The CT system also includes a stationary structure communicatively coupled to the rotational gantry via one or more slip rings that transfer the processed image data from the rotational gantry to stationary memory integral with the stationary structure via a bidirectional serial data exchange protocol.

In another embodiment, a computed tomography (CT) system controller is configured to acquire image data by passing X-rays beams through a subject and detecting the X-rays beams with a detector. The controller is also configured to perform either lossy and/or lossless compression of the image projection data on a rotating gantry to generate compressed data, store the compressed data to non-volatile memory located on the rotating gantry, and transfer the compressed data from the non-volatile memory on the rotating gantry to memory in a stationary computer via a bidirectional serial data exchange protocol run over one or more slip rings.

BRIEF DESCRIPTION OF THE DRAWINGS

These and other features, aspects, and advantages of the present invention will become better understood when the following detailed description is read with reference to the accompanying drawings in which like characters represent like parts throughout the drawings, wherein.

DETAILED DESCRIPTION OF THE INVENTION

Figure 1:
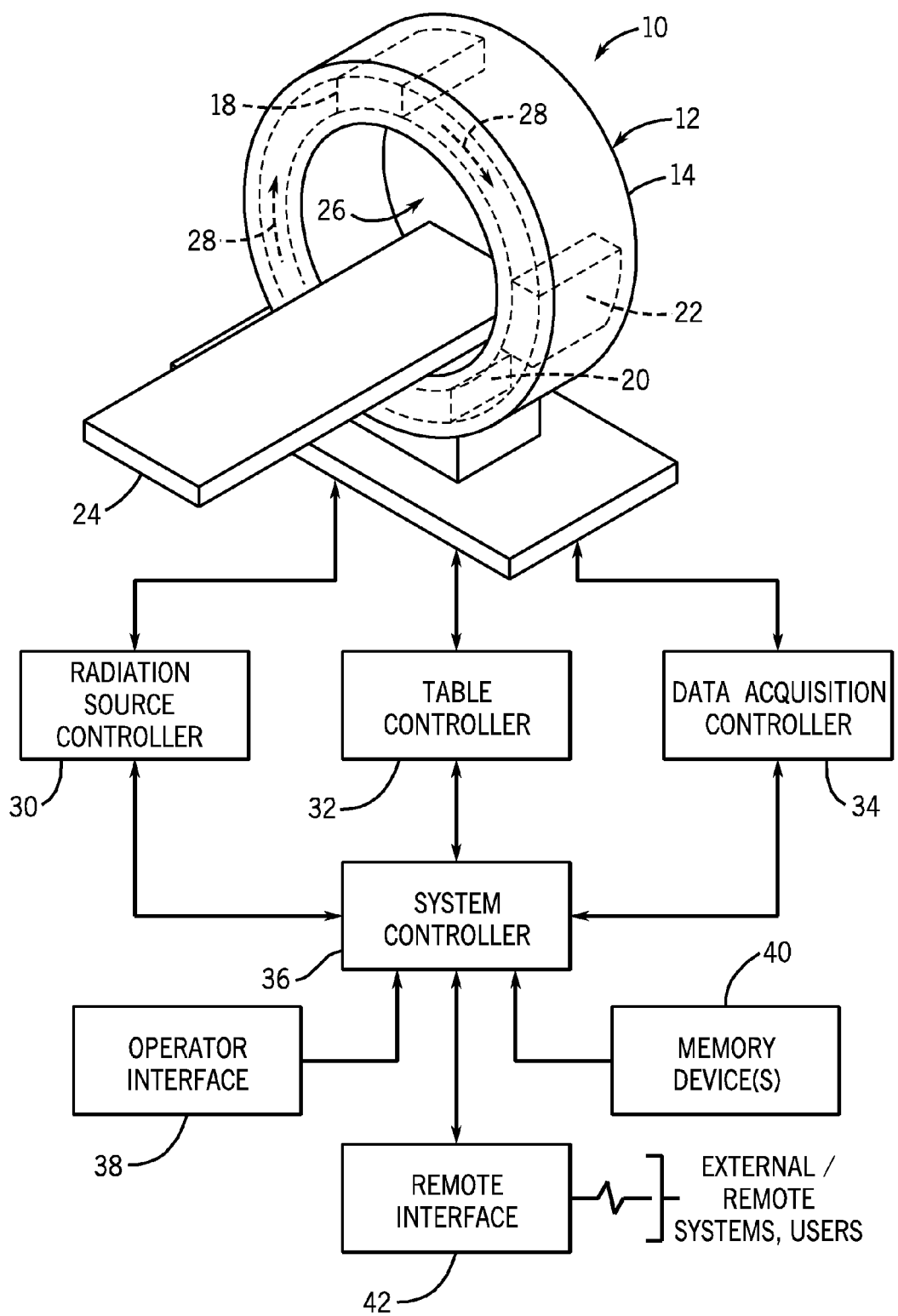
FIG. 1 is a diagrammatical representation of an embodiment of an exemplary CT system.

FIG. 1 illustrates an exemplary CT system 10 in which the invention is operative. The CT system 10 includes a scanner 12 including a stationary support structure 14 and a rotational gantry 16. An X-ray radiation source 18, a detector 20, and a data acquisition system 22 are disposed on the rotational gantry or rotating assembly 16. The X-ray radiation source 18 may emit various types and shapes of X-ray beams. These may include fan-shaped beams, cone-shaped beams, beams of various cross-sectional geometries, and the like, as well as beams of various energy levels. The scanner 12 is configured to receive a table 24 or other support for a subject (e.g., a patient) to be scanned. The table 24 can be moved through an aperture 26 in the scanner 12 to appropriately position the subject in an imaging volume or plane scanned during imaging sequences. Furthermore, the rotational gantry 16 is configured to rotate within the stationary structure 14 in the direction indicated by arrows 28 to acquire the desired data.

The CT system 10 further includes a radiation source controller 30, a table controller 32, and a data acquisition controller 34, which may all function under the direction of a system controller 36. The radiation source controller 30 regulates timing for discharges of X-ray radiation, which is directed from points around the scanner 12 toward the detector 20 on an opposite side thereof. In some embodiments, the radiation source controller 30 may trigger one or more emitters in a distributed X-ray source or transmission of radiation from multiple separate sources at each instant in time for creating multiple projections or frames of measured data. In certain arrangements, for example, the X-ray radiation source controller 30 may trigger emission of radiation in sequences so as to collect adjacent or non-adjacent frames of measured data around the scanner 12. Many such frames may be collected in an examination sequence, and data acquisition controller 34 receives signals from the detector 20 and processes the signals for storage and later image reconstruction. In certain embodiments, source controller 30 may also direct movement of the rotatable gantry 16 on which the distributed X-ray source 18 is mounted. In other embodiments, the data acquisition controller 34 may direct rotation of the rotatable gantry 16. Further, the table controller 32 serves to appropriately position the table 24 and subject in a plane in which the radiation is emitted. The table 24 may be displaced between imaging sequences or during certain imaging sequences, depending upon the imaging protocol employed.

System controller 36 generally regulates the operation of the radiation source controller 30, the table controller 32 and the data acquisition controller 34. For instance, the system controller 36 may cause radiation source controller 30 to trigger emission of X-ray radiation, as well as to coordinate such emissions during imaging sequences defined by the system controller 36. The system controller 36 may also regulate movement of the table 24 in coordination with such emission so as to collect measurement data corresponding to volumes of particular interest, or in various modes of imaging, such as helical or non-helical modes. Moreover, system controller 36 may coordinate rotation of the rotatable gantry 16 on which the X-ray source 18, the detector 20, and the data acquisition unit 22 are mounted. The system controller 36 also receives data acquired by data acquisition controller 34 and coordinates storage and processing of the data.

System controller 36 is also coupled to an operator interface 38 and one or more memory devices 40. The operator interface 38 may be integral with the system controller 36 and will generally include an operator workstation for initiating imaging sequences, controlling such sequences and manipulating measurement data acquired during imaging sequences. The memory devices 40 may be local to the imaging system, or may be partially or completely remote from the system. Thus, memory devices 40 may include local, magnetic or optical memory, or local or remote repositories for measured data for reconstruction. Moreover, the memory devices 40 may be configured to receive raw, partially processed or fully processed measurement data for reconstruction.

System controller 36 or operator interface 38, or any remote systems and workstations, may include software for image processing and reconstruction. Such processing of CT measurement data may be performed by a number of mathematical algorithms and techniques. For example, conventional filtered back-projection techniques may be used to process and reconstruct the data acquired by the imaging system. Other techniques, and techniques used in conjunction with filtered back-projection may also be employed. Additionally, a remote interface 42 may be included in the system for transmitting data from the imaging system to such remote processing stations or memory devices.

Figure 2:
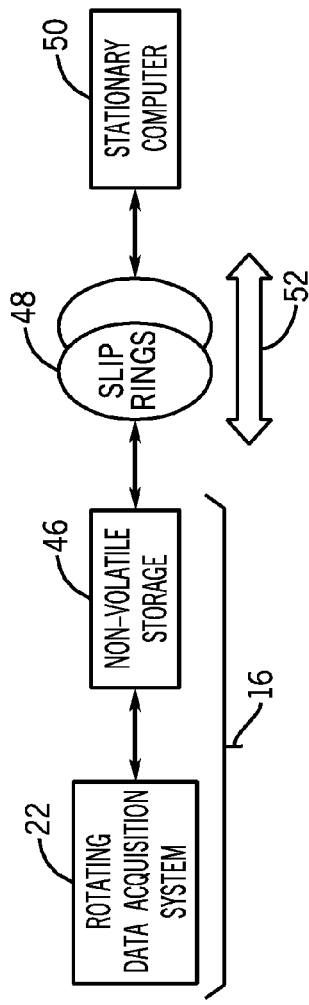
FIG. 2 is a block diagram illustrating an embodiment of an exemplary data flow through the CT system of FIG. 1.

FIG. 2 is a block diagram of an exemplary data flow through the CT system 10 of FIG. 1. As shown, imaging data is first received by the rotating data acquisition system 22. That is, after X-rays are emitted by the X-ray source 18, travel through the subject, and reach the detector 20, they are transferred to the data acquisition system 22, which is located on the rotatable gantry 16. As such, the data acquisition system 22 is configured to receive analog signals encoding projection data and to convert the analog signals into digital data for further processing. Accordingly, the data acquisition system may include a variety of suitable components, such as electrical circuitry that may, among other things, convert, compress and process the projection data. For example, the data acquisition system 22 may include data reduction circuitry configured to perform a lossy compression of the data. That is, in some embodiments, the present invention provides for lossy data reduction in the data acquisition system 22, which is mounted on the rotating assembly 16. Examples of the types of compression that may be employed include lossy and/or lossless compression. To this end, the data acquisition system 22 may include interface boards, control boards, transistors, rectifiers, and the like.

The data flow 44 also includes non-volatile storage 46 located on the rotatable gantry 16. That is, in presently contemplated embodiments, the non-volatile storage 46 may not be located on the stationary structure 14, but rather is located on the rotating gantry 16. The non-volatile storage 46 may be any storage unit type that is resistant to damage during movement of the rotating gantry 16 and capable of retaining stored data even when power is not available. For example, the non-volatile storage 46 may be any suitable solid state drive, such as a NAND flash solid state drive. The foregoing feature may offer advantages over systems in which the non-volatile storage 46 remains integral with a stationary portion of the CT system 10. For example, disclosed embodiments may reduce or eliminate the dependency of the CT system on one or more slip rings, which may be unreliable during operation. Furthermore, the one or more slip rings in disclosed embodiments need not be capable of data transfer speeds as high as previous systems since the non-volatile storage 46 provides a permanent storage unit on the rotating gantry 16.

The data flow 44 also includes one or more slip rings 48 capable of transmitting data from the rotating gantry 16 to one or more stationary system components that are located in a stationary computer 50. To that end, the slip rings 48 are electrically connected to the rotating gantry 16 and suitable contacts (e.g., brushes) mounted on the stationary structure 14 contact the slip rings 48, thus transferring data from the slip rings 48 to the stationary computer 50. In the illustrated embodiment, a bidirectional serial data exchange protocol 52 is run over the slip rings 48 and facilitates the bidirectional exchange of data to and from the slip rings 48. For instance, the data exchange protocol 52 may allow the concurrent bidirectional exchange of data between the slip rings 48 and the stationary computer 50, the slip rings 48 and the non-volatile storage 46, and so forth. That is, the data exchange protocol 52 allows for data to be exchanged both to and from the slip rings 48 at the same time.

In some embodiments, the bidirectional serial data exchange protocol 52 may be any suitable protocols, such as a protocol commonly referred to as the "Peripheral Component Interconnect Express" or "PCI Express" protocol cooperatively developed by several commercial organizations, including Intel, of Santa Clara, Calif. Versions of the protocol include PCI Express 1.0, PCI Express 2.0, PCI Express 2.1, PCI Express 3.0. Other protocols may be employed as well. In such embodiments, advantages may be gained over systems that do not employ bidirectional serial data exchange protocols. For example, the serial data exchange protocols 52 provide the ability to transfer data between system components without the drawbacks of conventional parallel connections. Specifically, because serial data exchange protocols 52 provide switches that may control a plurality of serial connections, each system component that communicates with the slip rings 48 has its own dedicated connection and does not share bandwidth with any other system components. As compared to conventional systems, the foregoing features of the disclosed embodiments may have the effect of increasing data transfer speeds, facilitating data exchange in two directions at the same time, and reducing system cost, among other things.

Figure 3:
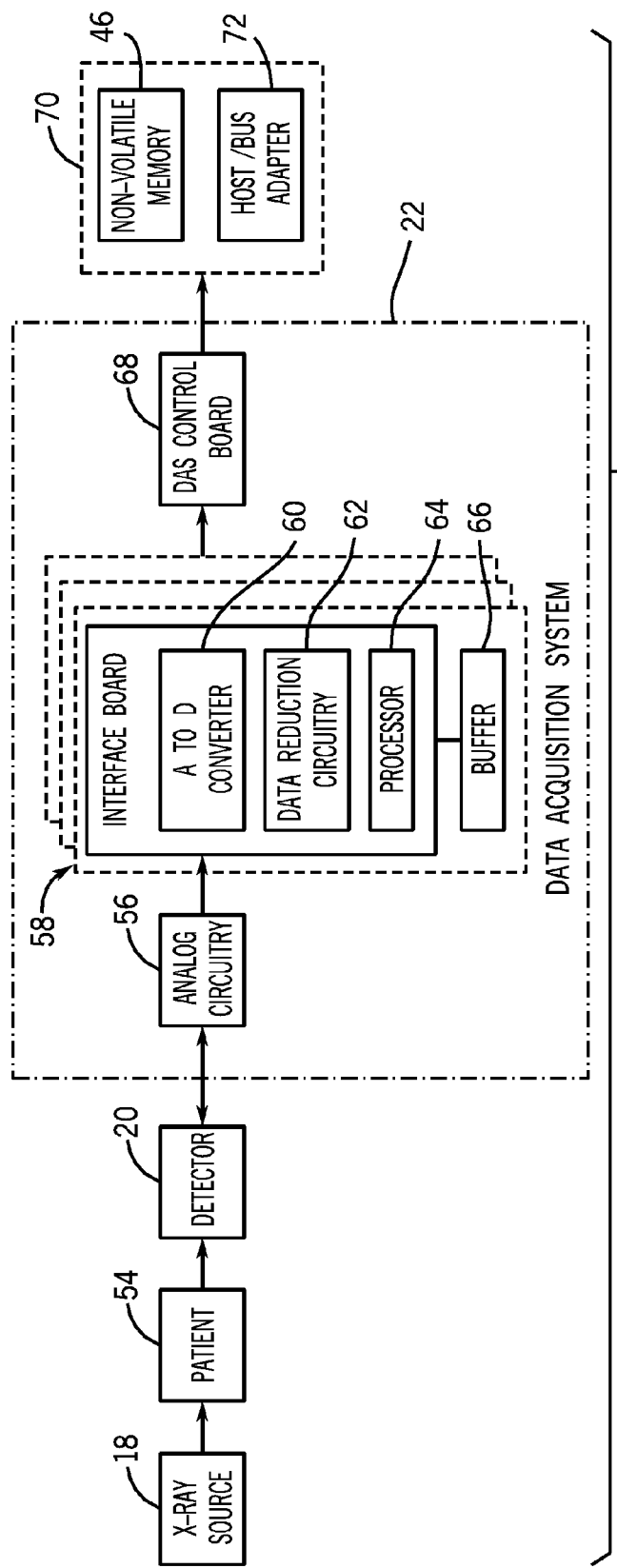
FIG. 3 is a block diagram of an embodiment of a data acquisition system located on a rotational gantry in the CT system of FIG. 1.

FIG. 3 illustrates exemplary components of one embodiment of the data acquisition system 22. In particular, FIG. 3 illustrates the X-ray source 18, which emits an X-ray beam that travels through a patient 54. The X-ray beam is attenuated by the internals of the patient 54, and attenuated X-rays emerge from the patient 54 and impact the detector 20. The detector 20 is generally formed by a plurality of detector elements that detect the X-ray beams after they pass through or around the patient 54. Each detector element produces an electrical signal that represents the intensity of the X-ray beam incident at the position of the detector element when the beam strikes the detector 20. Typically, the X-ray beam is generated and the corresponding electrical signals are acquired at a variety of angular positions around the patient 54 so that a plurality of radiographic projection views can be collected.

The electrical signals from the detector 20 are transferred to analog circuitry 56 located in the data acquisition system 22. The analog circuitry 56 includes electrical elements capable of encoding analog signals (i.e., capable of encoding the continuous voltage and current of the entire incoming signal). To this end, the analog circuitry 56 may include active electrical elements as well as passive electrical elements (e.g., inductors, capacitors, resistors). In certain embodiments, the analog circuitry 56 transfers the analog signals encoding projection data to one or more interface boards 58 located in the data acquisition system 22. Each interface board 58 may be configured to receive and handle data from a subset of the detector elements in the detector 20. For example, in one embodiment, the detector may include 100 detector elements, and 10 interface boards may be configured to each handle data from a subset of 10 detector elements. In further embodiments, the interface boards 58 may each be configured to handle data from the same number of detector elements (e.g., each board handles 10 detector elements) or unequal numbers of detector elements (e.g., some boards handle 10 elements each while others handle 15 elements each). Indeed, any suitable number of interface boards 58 may be used to handle the data from any quantity of detector elements in the detector 20.

Each interface board 58 includes a variety of functional components. In the illustrated embodiment, each interface board 58 includes an analog to digital converter (ADC) 60, data reduction circuitry 62, and a processor 64. Additionally, each interface board may be connected to a buffer 66. The ADC 60 may be any suitable electronic device capable of converting the incoming continuous analog signal from the analog circuitry 56 to a discrete digital signal. During operation, after analog to digital conversion, the digital signal is transmitted to the data reduction circuitry 62, which is configured to compress the digital data by reducing the number of bits necessary to encode the signal. The processor 64 is configured to receive and process the compressed data for further transmission to other system components. For example, the processor 64 may control the management of one or more application specific integrated circuits (ASICs). The buffer 66 may also be included to ensure that acquired data is temporarily stored while it is being processed in the data acquisition unit 22 on the rotatable gantry 16 but before it is transferred to the stationary structure 14, as discussed in more detail below.

The data acquisition unit also includes a data acquisition control board (DCB) 68 that receives processed digitized data from each of the interface boards 58. The DCB 68 sorts and assimilates the data from the interface boards 58. That is, the DCB 68 aggregates and consolidates the data from all the interface boards 58 into a single stream of data suitable for further transmission out of the data acquisition unit 22. Data exiting the data acquisition unit 22 is transferred to an interface unit 70 located on the rotatable gantry 16. The interface unit 70 includes the non-volatile memory 46 and a host bus adapter 72. Data is stored to the non-volatile memory 46 on the gantry 16 as it is acquired and processed. In certain embodiments, the non-volatile memory 46 may be permanent (i.e., not removable from the gantry 16). Furthermore, while the data is stored to the non-volatile memory 46 as it is acquired, it may be retrieved from the memory 46 at a later point in time, albeit not through removal of the memory 46 from the gantry 16. The host-bus adapter 72 is configured to communicatively couple the stationary computer 50 to other system devices by facilitating a connection between the computer 50 and other components.

Figure 4:
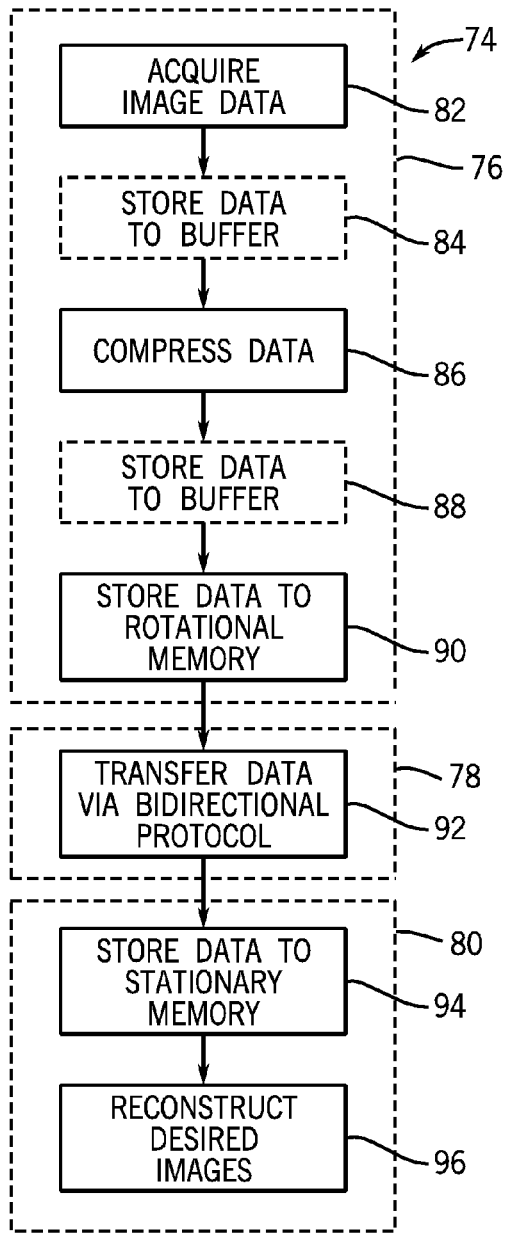
FIG. 4 is a flow chart illustrating an exemplary image acquisition method for use with the CT system of FIG. 1.

FIG. 4 is an image acquisition flow chart 74 that may be used in conjunction with the CT system 10 of FIG. 1 to acquire, process, and reconstruct image data. The image acquisition method 74 includes a first set of steps 76 performed by components located on the rotatable gantry 16, a second set of steps 78 performed over the slip rings 48, and a third set of steps 80 performed by components of the stationary structure 14. First, the system acquires the image data (block 82) by subjecting the patient to X-rays from the X-ray source. The system may then store the acquired data to the buffer 66 if desired (block 84). Next, either lossy and/or lossless compression is performed on the data (block 86). That is, lossy data compression may be performed such that some loss of data is tolerated as long as the essential nature of the data is preserved. The use of lossy compression may offer distinct advantages over other systems. For example, the storage capacity on the rotatable gantry 16 may be increased with minimal loss of image quality when lossy compression is employed since nonessential bits may be discarded. After data compression, the system may again store the acquired data to the buffer 66 if desired (block 88). Some embodiments may include only buffer step 84, only buffer step 88, both, or neither. The compressed data is then stored to the non-volatile memory located on the rotational gantry 16 (block 90).

Once the data is stored to the non-volatile memory on the rotatable gantry 16, the data may be transferred over the slip rings via any of a variety of bidirectional serial data exchange protocols as discussed in detail above (block 92). As the data is transferred over the slip rings, it is stored to stationary memory integral with the stationary structure 14. It should be noted that while the data is stored to the rotational memory (block 90) as it is acquired from the patient, it may be stored to the stationary memory (block 94) at a much slower rate. Indeed, in some embodiments, the data may not be completely stored to the stationary memory until after the imaging data has been fully acquired from the patient. In some embodiments, once the data has been fully transferred to the stationary memory, images of the desired anatomy are reconstructed (block 96).

Figure 5:
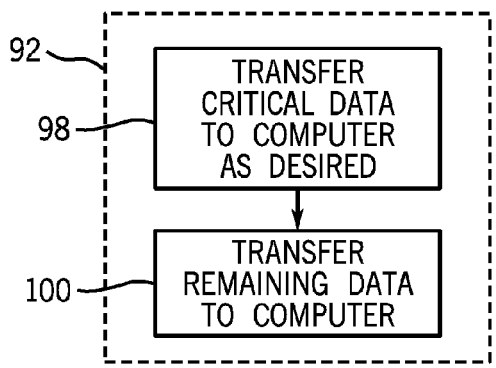
FIG. 5 is a flow chart illustrating an embodiment of the data transfer step of the image acquisition method of FIG. 4.

FIG. 5 illustrates an embodiment of the data transfer step 92 of the image acquisition flow chart 74 of FIG. 4. In this embodiment, rough images based on partial data sets may be reconstructed and viewed by a user prior to complete transfer of the data to the stationary memory. Specifically, critical data is transferred to the stationary memory in the computer during data acquisition (block 98). For example, in one embodiment, every third slice may be immediately transferred while the intermittent slice may be transferred at a later time. In other embodiments, only the data corresponding to one critical area of the patient anatomy may be immediately transferred. The foregoing feature may provide the user with visual confirmation that the CT scan is proceeding properly. In such embodiments, the remaining data may is transferred to the computer only after the critical data transfer is complete (block 100).

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The Invention claimed is:

1. A computed tomography (CT) system, comprising:
   a rotational gantry comprising:
   an X-ray source configured to emit an X-ray beam through a subject;
   an X-ray detector comprising one or more detector elements configured to receive incoming X-rays and to convert the incoming X-rays to image signals;
   a data acquisition unit comprising data reduction circuitry configured to perform lossy, lossless, or both lossy and lossless compression of the image signals to generate compressed image data, and wherein the data acquisition unit comprises a data acquisition control board configured to consolidate the compressed image data from a plurality of interface boards into a single stream and to provide the single stream of compressed image data to a non-volatile memory device, wherein each interface board is configured to receive image signals from a different subset of the detector elements;
   the non-volatile memory device configured to store the compressed image data; and
   a stationary structure communicatively coupled to the rotational gantry via one or more slip rings configured to transfer the compressed image data from the rotational gantry to stationary memory integral with the stationary structure.

2. The CT system of claim 1, comprising a bidirectional serial data exchange protocol running over the one or more slip rings.

3. The CT system of claim 2, wherein the bidirectional serial data exchange protocol is a peripheral component interconnect protocol.

4. The CT system of claim 1, wherein the data acquisition unit comprises an analog to digital converter configured to convert the image signals from an analog image signal to a digital image signals.

5. The CT system of claim 1, wherein the data acquisition unit comprises a buffer configured to buffer the image signals.

6. The CT system of claim 1, wherein the compressed image data is transferred from the rotational gantry to the stationary memory integral with the stationary structure after image acquisition is complete.

7. The CT system of claim 1, wherein each interface board of the plurality of interface boards comprises data reduction circuitry.

8. A computed tomography (CT) system, comprising:
   a rotational gantry comprising:
   an X-ray source configured to emit an X-ray beam through a subject;
   an X-ray detector comprising one or more detector elements configured to receive incoming X-rays and to convert the incoming X-rays to image signals;
   a data acquisition unit configured to process the image signals to generate processed image data, wherein the data acquisition unit comprises a data acquisition control board configured to consolidate the processed image data from a plurality of interface boards into a single stream for transmission out of the data acquisition unit, wherein each interface board is configured to receive image signals from a different subset of the detector elements; and
   a stationary structure communicatively coupled to the rotational gantry via one or more slip rings configured to transfer the processed image data from the rotational gantry to stationary memory integral with the stationary structure via a bidirectional serial data exchange protocol comprising a peripheral component interconnect protocol.

9. The CT system of claim 8, wherein the data acquisition unit comprises data reduction circuitry configured to perform lossy compression of the image data.

10. The CT system of claim 9, wherein each interface board of the plurality of interface boards comprises data reduction circuitry.

11. The CT system of claim 8, wherein the data acquisition unit comprises a buffer configured to buffer the image data.

12. The CT system of claim 8, comprising a non-volatile memory device that stores the processed image data.

13. The CT system of claim 12, wherein the non-volatile memory device is disposed on the rotational gantry.

14. A computed tomography (CT) system controller configured to:
   acquire image data by passing X-ray beams through a subject and detecting the X-ray beams with a detector comprising one or more detector elements that convert the detected X-ray beams to image signals;
   perform lossy compression of the image data on a rotating gantry to generate compressed image data;
   store the compressed image data to non-volatile memory located on the rotating gantry, wherein a data acquisition unit located on the rotating gantry comprises a data acquisition control board that consolidates the compressed image data from a plurality of interface boards into a single stream and provides the single stream of compressed image data to the non-volatile memory, wherein each interface board receives image signals from a different subset of the detector elements;
   transfer the compressed image data from the non-volatile memory on the rotating gantry to memory in a stationary computer via a bidirectional serial data exchange protocol run over one or more slip rings.

15. The CT system controller of claim 14, wherein the bidirectional serial data exchange protocol is a peripheral component interconnect protocol.

16. The CT system controller of claim 14, wherein the CT system controller is configured to reconstruct one or more images based on the compressed image data.

17. The CT system controller of claim 14, wherein the CT system controller is configured to buffer the image data.

18. The CT system controller of claim 14, wherein the CT system controller is configured to transfer a critical portion of the compressed image data to the stationary computer immediately during acquisition.

19. The CT system controller of claim 18, wherein the CT system controller is configured to transfer a non-critical portion of the compressed image data to the stationary computer after acquisition.

20. The CT system controller of claim 14, wherein the CT system controller is configured to transfer all of the compressed image data to the stationary computer immediately during acquisition.

* * * * *